Figure 1:
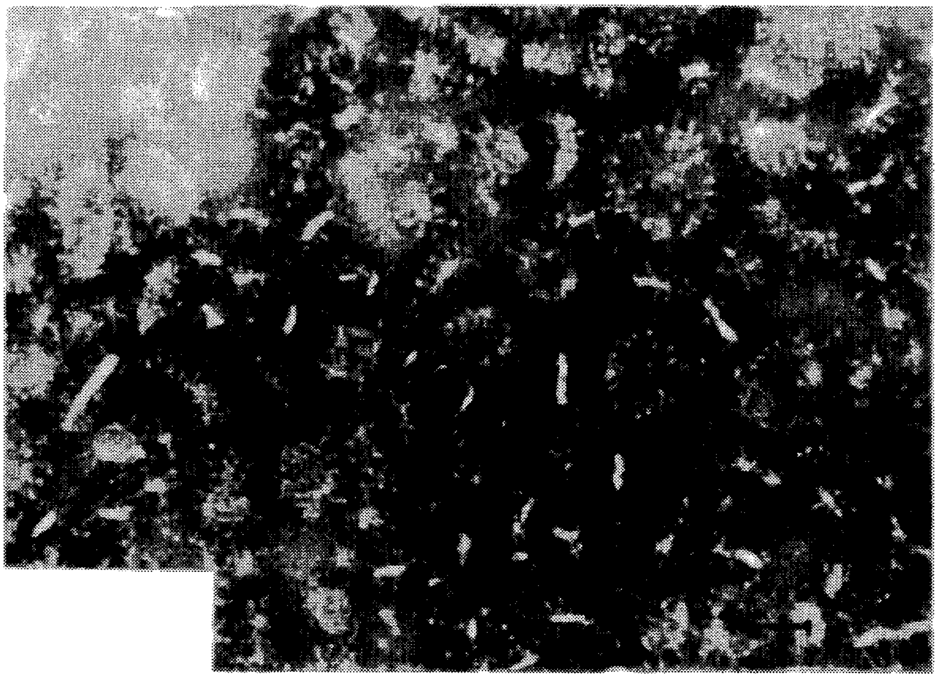

US005565203A

United States Patent [19]

Glück et al.

[11] Patent Number: 5,565,203

[45] Date of Patent: Oct. 15, 1996

[54] HEPATITIS A VIRUS IN A RECONSTITUTED INFLUENZA VIROSOME AND USE AS A VACCINE

[75] Inventors: Reinhard Glück, Spiegel/Bern; Robert Mischler, Worblaufen, both of Switzerland

[73] Assignee: Schweiz. Serum- & Impfinstitut Bern, Bern, Switzerland

[21] Appl. No.: 965,246

[22] Filed: Mar. 3, 1993

[30] Foreign Application Priority Data

May 8, 1991 [EP] European Pat. Off. .............. 91107527
May 10, 1991 [EP] European Pat. Off. .............. 91107647

[51] Int. Cl.$^6$ .......................... A61K 39/29; A61K 45/00; A61K 47/44; A61K 9/133

[52] U.S. Cl. .................................... 424/226.1; 424/278.1; 424/281.1; 424/283.1; 424/450

[58] Field of Search ............................... 424/89, 88, 450, 424/226.1, 283.1, 281.1, 278.1

[56] References Cited

U.S. PATENT DOCUMENTS

| | | | |
|---|---|---|---|
| 4,148,876 | 4/1979 | Almeida et al. | 424/450 |
| 4,199,565 | 4/1980 | Fullerton et al. | 424/450 |
| 4,663,161 | 5/1987 | Mannino et al. | 424/450 |
| 4,731,237 | 3/1988 | Reagan et al. | 424/131.1 |

FOREIGN PATENT DOCUMENTS

| | | |
|---|---|---|
| 0011549 | 5/1980 | European Pat. Off. . |
| 0047480 | 3/1982 | European Pat. Off. . |
| 0356339 | 2/1990 | European Pat. Off. . |

OTHER PUBLICATIONS

Hughes et al, J. Virol. 55(2):395–401, 1985.
Seganti et al, Microbiologica 12(3) 225–30, 1989 (abstract only included).
Harter et al. J. Biol. Chem. 264(11):6459–6464, 1989.
Mortimer E A, "Diptheria Toxoid" in *Vaccines.*
Plotkin et al eds. W. B. Saunders Co. 1988 p. 39.
Alving et al, Vaccine 4(3) 166–172, 1986.
Binn et al, J. of Infect. Dis. 153(4):749–756, 1986.
Boslego et al "Gonorrhea Vaccines" in *Vaccines and Immunotherapy*, S. J. Cryz ed. Pergamon Press, 1991 p. 211–223.
Kallings et al, Lancet I: 955–960, 1988.
Manesis et al, FEBS Letters 102(1):107–111, 1979.
Hackett et al, Immunology 49:255–263, 1983.

*Primary Examiner*—James C. Housel
*Assistant Examiner*—Julie Krsek-Staples
*Attorney, Agent, or Firm*—Greenblum & Bernstein, P.L.C.

[57] ABSTRACT

Disclosed are immunostimulating reconstituted influenza virosomes (IRIVs) comprising reconstituted functional virus envelopes containing an inactivated hepatitis A virus and an influenza hemagglutinin protein (HA) or a peptide with the amino terminal 21 amino acid residue segment of $HA_2$ which induces the fusion of the IRIVs with cellular membranes and the lysis of the IRIV. A vaccine containing the hepatitis A IRIVs is also disclosed.

10 Claims, 4 Drawing Sheets

Biological fusion activity of different reconstituted influenza vesicles

HEPATITIS A VIRUS IN A RECONSTITUTED INFLUENZA VIROSOME AND USE AS A VACCINE

The invention relates to immunostimulating and immuno-potentiating reconstituted influenza virosomes (IRIVs) and to vaccines containing them.

A large range of procedures to enhance immunogenicity has been developed over several decades by measures that retain a considerable empirical element. The most potent methods (e.g. administering the immunogen together with Freund's complete adjuvant) combine a number of the separate principles explained in the following sections:

(A) Rendering the antigen particulate

Particles are more attractive to macrophages than soluble antigens and tilt the balance in favor of immunity rather than suppression. Particle formation can vary from a simple heat-induced aggregation to sophisticated polymerization strategies, including the self-aggregation characteristic of antigens, such as the soluble antigen of hepatitis B virus. In the case of liposomes or oily droplets, there is a combined effect of particulateness and slow absorption, such as with alum precipitation.

(B) Chemical immunopotentiation

A long history of research underlies the search for a pure, safe, effective, nontoxic small organic molecule which mimics the potentiation of the whole immune response that can be achieved with killed *Mycobacterium tuberculosis* bacteria or toxic microbial extracts, such as *E. coli* LPS. No uniformly approved satisfactory agent has been found for use in humans and a disconnection of toxicity and efficacy is difficult to achieve.

(C) Co-administration with interleukins

There is some evidence that the co-administration of, for example, IL-2 with an antigen can result in a greater enhancement of the immune response than the separate administration of the antigen and the interleukin; see Staruch, M. J. and Wood, D. D., J. Immunol. 130 (1983), 2191. Before this approach becomes feasible as an immunization strategy in humans, it requires further extensive investigations. However, it may be rendered obsolete by the suggestions included in the following sections.

(D) Slowing down the release of the immunogen

The sudden application of large doses of pure protein antigens includes the risk of activating the suppressor pathways in the immune responses, particularly if the intravenous route is used; see Nossal, G.J.V., New Generation Vaccines, Marcel Dekker, Inc. New York, Basle (eds. Woodrow, Levine), (1990) 85. Slow release from a subcutaneous depot site permits extensive access of the antigen to the widely scattered dendritic cells and macrophages, and it also ensures that antigen will still be available after the initial burst of clonal proliferation, thereby permitting some facets of a secondary response. Slow release is favored by adsorbing antigens onto aluminum hydroxide ("alum precipitation"); placing antigens into water-in-oil emulsions; incorporating antigens into liposomes; and other similar manipulations. This method is conceptually close to the one described in section A.

(E) Co-exhibition of the antigens with a highly immunogenic agent

If a particular vaccine is highly immunogenic, the adjuvant effect of this vaccine, and also the characteristics it may possess for guiding the response toward a particular immunological pathway, may "spill over" into a response to an antigen co-administered with it. For example, killed *Bordetella pertussis* or *Corynebacterium parvum* bacteria are powerful immunogens; if a pure protein is administered with the same injection, the response to it is enhanced. Certain immunogens (for reasons that are unclear) guide the response in particular directions. For example, extracts of a parasite, such as *Nippostrongylus brasiliensis,* elicit powerful IgE responses. Pure proteins co-administered with the parasite extracts will also evoke an IgE response; see Nossal, G.J.V., New Generation Vaccines, Marcel Dekker, Inc. New York, Basle (eds. Woodrow, Levine), (1990) 85. Presumably, this effect is somehow connected to the production of particular lymphokines which is induced by particular agents. Said lymphokines, such as IL-4, guide isotype switch patterns. The polyclonal activating characteristics of lymphokines may also form the basis for the enhancement of immune responses in general.

(F) Genetically engineered microorganisms as carriers of genes for important antigens The notion of genetically engineered microorganisms as antigen gene carriers was pioneered by Panicali, D. and Paoletti, E.: *Proc. Natl. Acad. Sci. USA,* 79 (1982), 4927, and Smith, G. L., Macket, M. and Moss, B. *Nature* 302 (1983), 490, who genetically engineered the genome of the vaccinia virus to additionally include genes coding for important host-protective antigens of various pathogens. These are synthesized by the infected cell together with vaccinia virus particles and antigens. An improvement of this concept was introduced by Langford, C. J., Edwards, S. J., Smith, G. L. et al., *Mol. Cell. Biol.* 6 (1986), 3191. With the idea in mind that cell surface-associated antigens are more likely to evoke a strong T cell response than secreted antigens, they linked a DNA sequence encoding the transmembrane domain of an immunoglobulin heavy chain to the gene encoding the soluble S antigen of *Plasmodium falciparum,* and inserted the resulting hybrid gene into the genome of a vaccinia virus. The construct caused a significantly enhanced immunogenicity. Live Salmonella, BCG and measles virus have also been successfully used for the expression of foreign antigen. Thus, the advantages of a live attenuated vaccine can be combined with those of a vaccine based on viruses containing recombinant DNA.

A further development of this idea is to insert genes for various interleukins into genetically engineered vaccinia viruses already carrying genes for important antigens. For example, the immune response to vaccinia virus itself can be markedly enhanced by the insertion of the IL-2 gene into the viral genome, permitting immunodeficient mice to recover from an otherwise fatal infection (Ramshas, I. A., Andrew, M. E., Philips, M. et al.; *Nature* 329 (1987), 545).

(G) Hydrophobic anchors and immunostimulating complexes

Surface-active agents such as saponin or Quil A \ in immunostimulating complexes (iscoms) have been used in a number of experimental and veterinary vaccines. They improved the immunogenicity of several antigens, especially of viral membrane proteins.

All of the above-mentioned "adjuvanting methods" have several disadvantages. Alum precipitation is disadvantageous because of the undesirable side effects such as local reactions, and its proinflammatory and encephalopathogenic potential. Surface-active agents display a number of side reactions: they are irritating, proinflammatory, they bind to cholesterol and lyse cells. Interleukins can provoke systemic reactions and therefore routine use in mass vaccination may be undesirable. Safety concerns prevented the use of genetically engineered microorganisms as carriers of genes for important antigens in man. Co-exhibition of the antigen with a highly immunogenic agent is only feasible with a limited class of small peptides. Rendering the antigen particulate often goes in parallel with a significant loss of the amount of antigen. The immunostimulatory effect of liposome-associated antigen on the humoral response is a widely recognized phenomenon, but immunopotentiation is limited and the mechanism by which this potentiation occurs is not totally elucidated at present.

Thus, the technical problem underlying the present invention is to provide immunostimulating and immunopotentiating agents which do not display the above-mentioned disadvantages.

The solution to the above technical problem is achieved by providing the immunostimulating reconstituted influenza virosomes (IRIVs) and vaccines containing said IRIVs which are characterized in the claims. These IRIVs can be used as vehicles which actively transport desired antigens of pathogens (or entire pathogens) to antigen presenting cells, such as macrophages or B cells, which then appropriately present said antigens to the immune system so as to induce an immune response.

Accordingly, IRIVs are provided which contain the following components:

(a) a mixture of phospholipids;

(b) essentially reconstituted functional virus envelopes;

(c) an influenza hemagglutinin (HA) or a derivative thereof which is biologically active and capable of inducing the fusion of said IRIVs with cellular membranes and of inducing the lysis of said IRIVs after endocytosis by antigen presenting cells, preferably macrophages or B cells; and (d) an antigen.

The "mixture of phospholipids" of feature (a) contains natural or synthetic phospholipids or a mixture thereof. At least it contains two different compounds selected from the group of glycero-phospholipids, such as phosphatidylcholine or phosphatidylethanolamine, and cholesterol. Phosphatidylcholine and phosphatidylethanolamine are preferred, in particular in a ratio of 4:1. In preferred embodiments of the present invention, the ratio of said mixture of phospholipids (a) to said essentially reconstituted functional virus envelopes (b) is about 1:1 to about 20:1. Most preferably it is about 10:1.

The term "essentially reconstituted functional virus envelopes" refers to reconstituted influenza virus envelopes which are essentially devoid of the components which naturally occur inside of (below) the influenza virus envelope's membrane part. In a preferred embodiment the essentially reconstituted functional virus envelopes exhibit the form of a unilamellar bilayer. An example of such a lacking component is the matrix protein of the natural influenza virus envelope.

The term "biologically active HA or derivative thereof" as components of the IRIVs of the present invention refers to HAs or derivatives which substantially display the full biological activity of native HA and are thus capable of mediating the adsorption of the IRIVs of the present invention to their target cells via sialic acid-containing receptors. Furthermore, such HA components can be recognized by circulating anti-influenza antibodies. This biological activity is an essential feature of the IRIVs of the present invention.

Thus, the function of the HA component of the IRIVs of the present invention may be explained as follows:

(1) it binds to a sialic-acid (N-acetylneuramininc acid) containing receptor on a target cell to initiate the virosome-cell interaction; and (2) it mediates the entry of the IRIVs into the cytoplasm by a membrane-fusion event and thus finally leads to the release of the transported antigen;

(3) it serves as a "recognition antigen" since most humans can be considered "primed" to HA due to prior exposure through disease or vaccination.

Thus, the essential feature of the IRIVs is that they carry on their surface beside the antigen said biologically active viral glycoprotein (HA) or derivative thereof. This component of the IRIVs of the present invention induces their immediate fusion with cellular cytoplasmic membranes and a quick release of the transported antigen, e.g. into the membranes of said cells. Thus, an undesired long stay of the transported antigen in the endocytosomes where they may be unspecifically degraded is avoided.

The fact that an antigen should be palatable for macrophages and other accessory cells is paramount. For this purpose, the particulate nature of the IRIV is advantageous since it is, like all microorganisms, a particulate entity. The presence of antibody in human bodies (in the case of influenza, all human beings have antibodies against influenza antigen. These antibodies originate either from a previous influenza infection or from a vaccination) speeds entry of antigens recognized by said antibodies not only into macrophages but also into lymphoid follicles, in which antigens are retained long-term in an extracellular location on the surface of follicular dendritic cells. This process of entering macrophages and lymphoid follicles is called opsonisation.

Binding by antibody has another consequence for the immunogenicity of antigens. Whereas a given antigen, A, in solution will only bind to B cells exhibiting antibody molecules of the specificity anti-A on their surface, immune complexes can adhere to any B cell via the Fc-receptor. Due to the capacity of B cells in afferent lymph vessels to enter B cell areas of lymph nodes, this unspecific binding via the Fc receptor is probably one route, in a natural infection, by which said antigen is transported to lymphoid follicles and elsewhere in lymphatic tissue (Nossal, G.J.V., New Generation Vaccines (ed. Woodrow, G. C. and Levine, M. M.), Marcel Dekker, Inc., (1990) 85. The mechanism would be an adjunct to the transport by monocytes. Hence, the presence of influenza antigens on the surface of the IRIVs favors the immunological mechanism of opsonization.

In one embodiment, the IRIVs of the present invention contain the complete HA which is synthesized as a single polypeptide chain of 550 amino acids which is subsequently cleaved by removal of arginine 329 into two chains, $HA_1$ (36,334 daltons) and $HA_2$ (25,750 daltons). These chains are optionally covalently linked by a disulfide bond involving the cysteine in $HA_1$ position 14 and the cysteine in $HA_2$ position 137 and the two-chain monomers are associated noncovalently to form trimers on the surface of IRIVs. These $HA_1$ or $HA_2$ peptides can be obtained from natural or synthetic sources or by genetic engineering.

In a preferred embodiment, the present invention relates to IRIVs wherein said antigen is derived from a pathogen including parts thereof. Preferred examples of such pathogens are a virus, a bacterium, a parasite, anti-idiotypic (Anti-Id) antibodies mimicking said viruses, bacteria or parasites, antibodies against said viruses, bacteria or parasites, or a toxin. Examples of viruses are hepatitis A, B, C, D or E virus, Polio virus, HIV, Rabies virus, Influenza virus or Parainfluenza virus. Examples of bacteria are Pseudomonas, Klebsiella, *E. coli, Salmonella typhi, Haemophilus influenzae, Bordetella pertussis, Clostridium tetani,* or *Corynebacterium diphtheriae.* An example of a parasite is *Plasmodium falciparum.*

In a particularly preferred embodiment of the present invention, said pathogen is a hepatitis A virus (HAV). A particularly preferred HAV is the HAV strain RG-SB XA112, which was deposited under the requirements of the Budapest Treaty at the Collection Nationale de Cultures de Microorganismes (CNCM) of the Pasteur Institute 28, rue du Dr Roux, 75724 Paris Cédex 15, France on Apr. 11, 1991, under the accession number I-1080. This deposit was made under the provisions of the Budapest Treaty on the International Recognition of the Deposit of Microorganisms for the Purpose of Patent Procedure and the Regulations thereunder (Budapest Treaty) on Apr. 11, 1991. This assures maintenance of a viable culture for 30 years from the date of deposit. The organism will be made available at Collection Nationale de Cultures de Microorganismes (CNCM) under the terms of the Budapest Treaty which assures permanent and unrestricted availability of the progeny of the culture to the public of any U.S. or foreign parent application, whichever comes first and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638).

In another preferred embodiment, the IRIVs of the present invention contain the structral proteins of hepatitis A virus VP1, VP2, VP3, VP4 or the core protein of said HAVs as the antigen.

In a further preferred embodiment of the IRIVs of the present invention, the antigen is located in the membrane. The inactivated HAV antigen or subunit thereof is optionally coupled to the surface of the IRIV. This can be achieved by covalently binding the antigen with a suitable crosslinker molecule (e.g. N-succinimidyl 3-(2-pyridyldithio) propionate, SPDP) or by spontaneous lipophilic binding to various phospholipids or glycolipids in the membrane of the IRIV.

In a further preferred embodiment the antigen, preferably the inactivated HAV antigen or subunit thereof, is adsorbed onto the surface of IRIVs in a non-covalent manner.

In another preferred embodiment of the present invention, said antigen is located inside of the IRIVs. Several HAV particles of the strain RG-SB or soluble subunits thereof are enclosed by the reconstituted membrane of the IRIV. The antigen is in a soluble state within the core fluid of the IRIV.

In a further preferred embodiment of the present invention, said HA derivative is the influenza HA fusion peptide. Since the fusion of the antigen carrier, IRIV, with the cell membrane of the immuno-competent cells is a fundamental principle of the present invention, the influenza HA fusion peptide alone is sufficient to induce the release of the antigen. This is because the release occurs at the pH value which is characteristic of the interior of endocytosomes. The pH in the endocytosomes, e.g. in macrophages, has been determined to be about 5.0 (Wiley, D. C. and Skehel, J. J., Ann. Rev. Biochem. 56 (1987), 365). At pH 5, the influenza HA fusion peptides on the surface of the IRIVs are activated in the same way as in case of the natural influenza virus.

In another embodiment, the present invention relates to a vaccine containing an IRIV of the present invention. Optionally, these vaccines additionally contain a suitable pharmaceutically acceptable carrier and/or diluent. These vaccines can be administered in conventional routes and dosages.

The Figures show:

FIG. 1: Electron micrograph of IRIV Electron micrographs of reconstitution products ducts negatively stained with phosphoting state before linking of the antigen to the surface of IRIVs: Mixed phospholipids are spiked with biologically fully active influenza enza hemagglutinin glycoprotein trimers.

Figure 2:
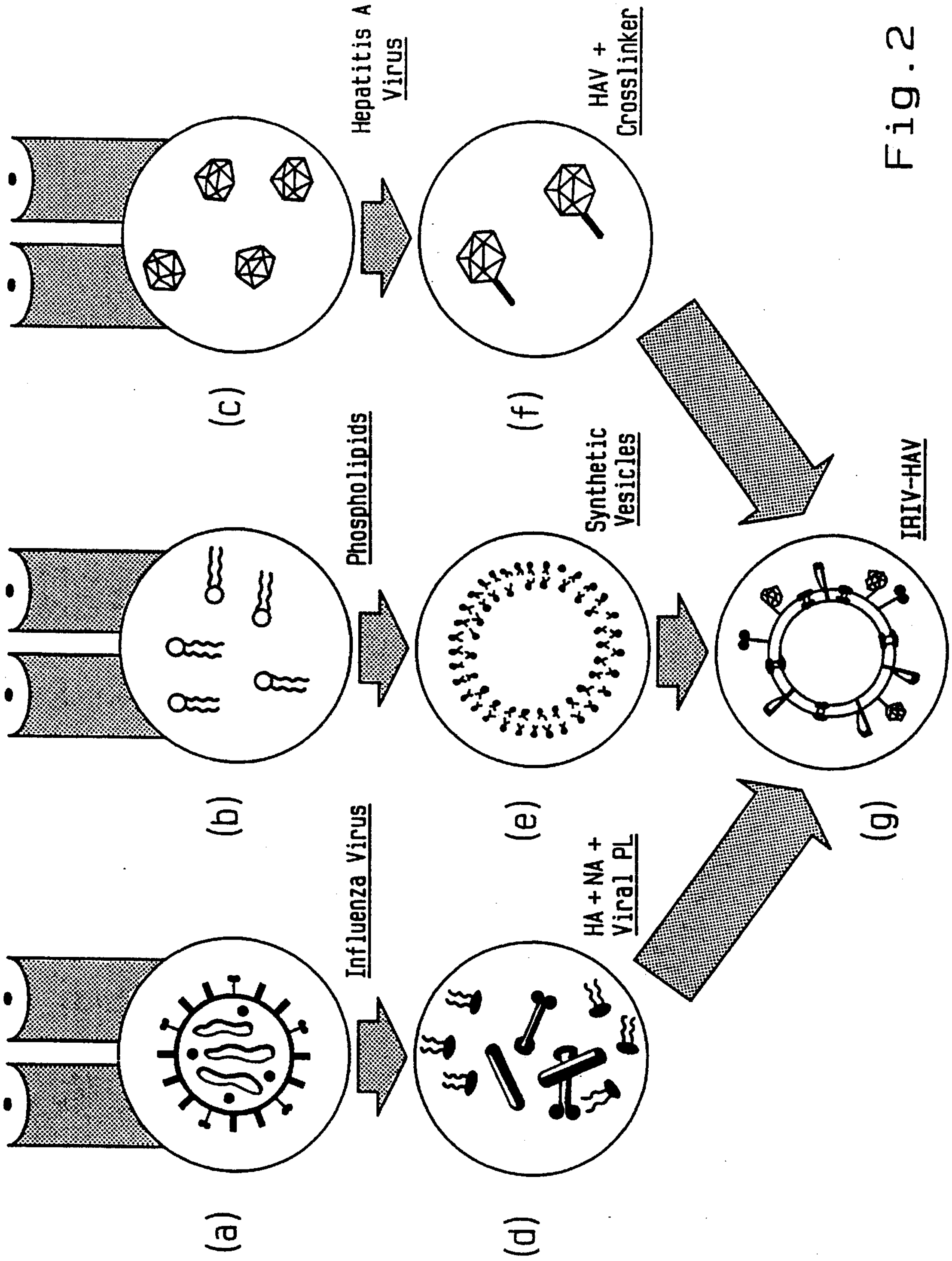

FIG. 2: Principle of the procedure of preparing IRIVs (a) intact influenza virus (b) mixture of phospholipids (c) intact, inactivated hepatitis A virions (d) soluble influenza spike subunit antigens containing the HA and viral phospholipids (e) phospholipid membranes without antigens (f) covalently bound cross-linkers on the surface of HAV antigen (g) IRIV containing the reconstituted membrane with phospholipids extracted from viruses and other phospholipids carrying the influenza spike proteins including HA and the HAV on the surface.

Figure 3:
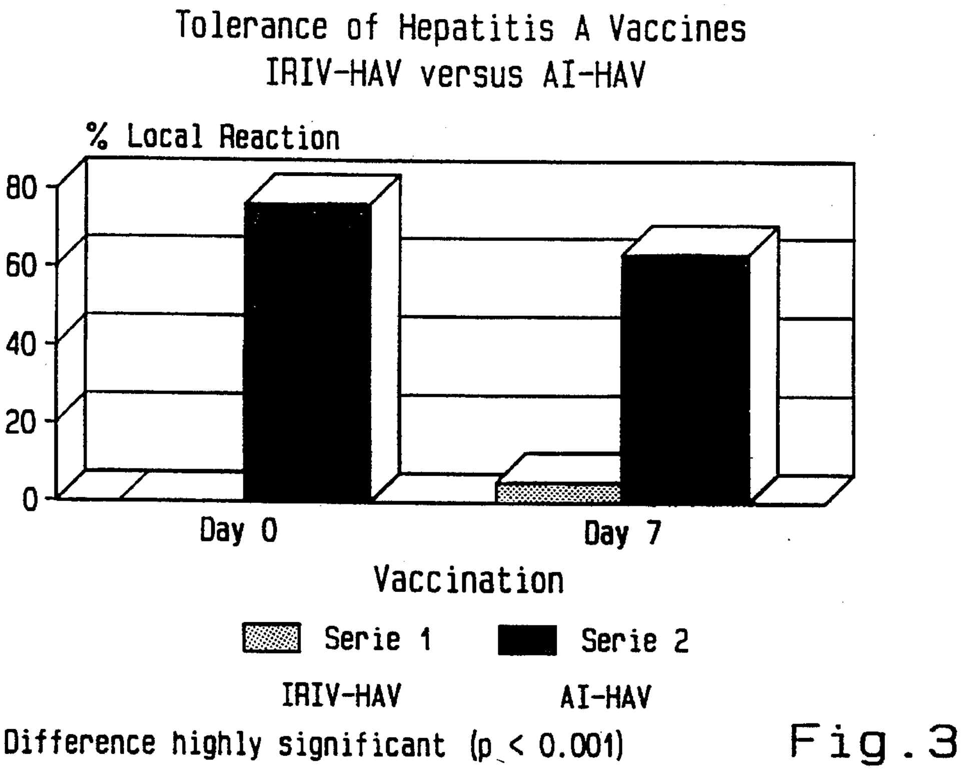

FIG. 3: Tolerance of hepatitis A vaccines. Comparison of IRIV-HAV vaccines versus Al-HAV vaccines.

Figure 4:
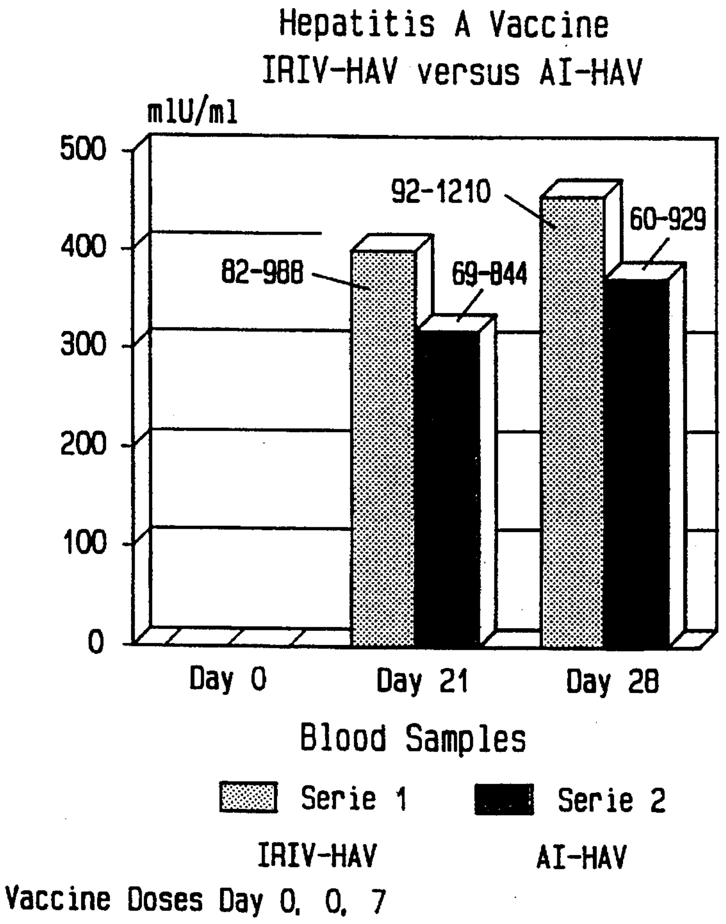

FIG. 4: Immunogenicity of hepatitis A vaccines. Comparison of IRIV-HAV vaccines versus Al-HAV vaccines.

Figure 5:
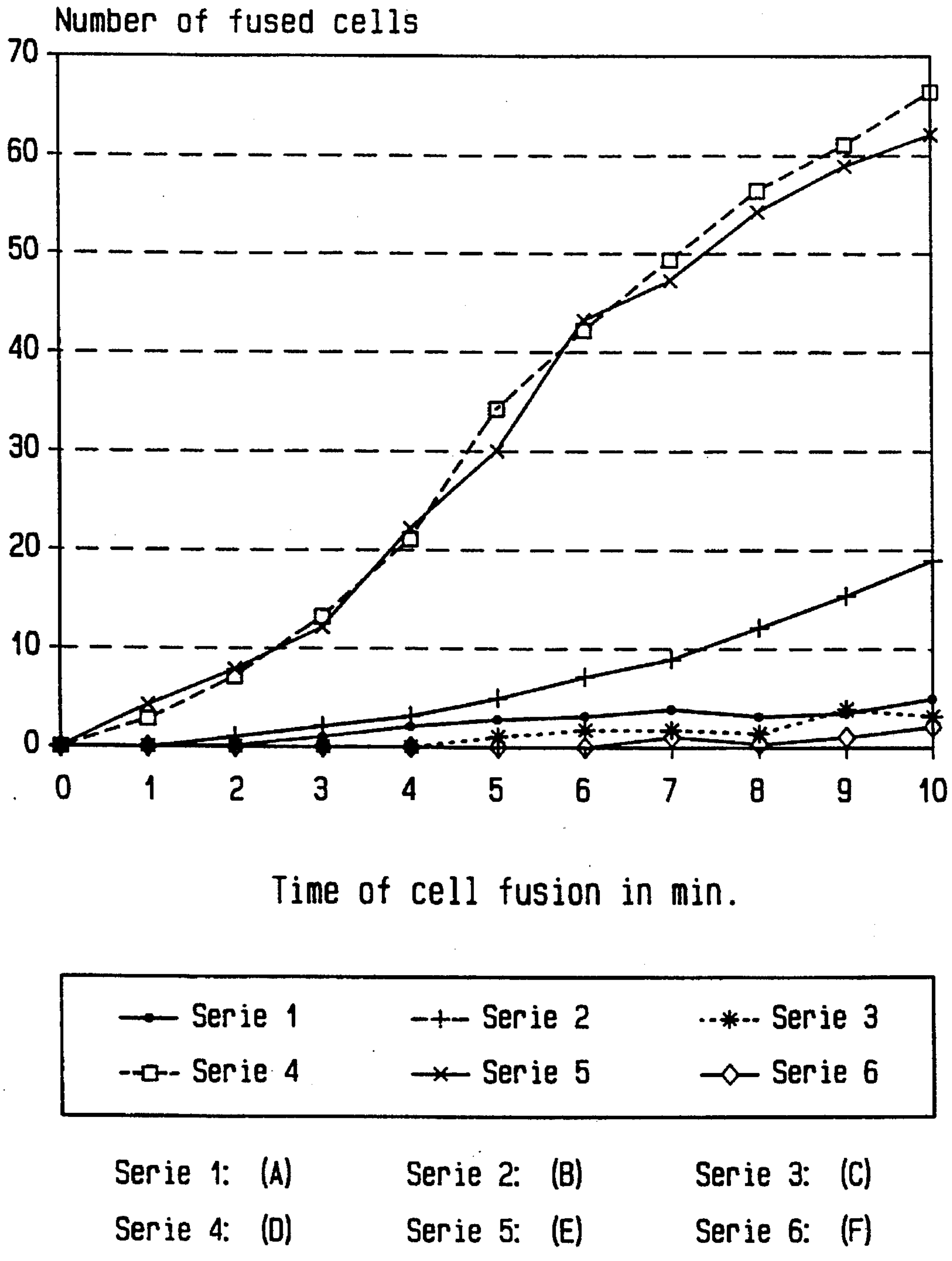

FIG. 5: Biological fusion activity of different reconstituted influenza vesicles.

The examples illustrate the invention.

EXAMPLE 1

Preparation of IRIVs with hepatitis A virus antigen non-covalently bound to their surface (A) A dispersion of phosphatidylcholine (e.g. lecithin, SIGMA) (75%), phosphatidylethanolamine (SIGMA) (20%) and cholesterol (SIGMA) (5%) (all phospholipids 1–2% (w/v)=0.013–0.027M) in 0.1M NaCl containing 0.01M Tris/HCl, pH 7.3 was prepared by mixing these compounds with a VIRTIS homogenizer. Sodium cholate recrystallized as the acid from acetone/water 4:1 (v/v) was added to the milky dispersion in a final concentration of at least 0.03M (1.3%) which is required to disintegrate the multilamellar structures present in unsonicated phospholipid dispersions.

A pellet of purified influenza virus 90 A/Taiwan (0.002M of viral membrane phospholipids) was solubilized in 700 ml of 0.1M Octaethyleneglycol mono(ndodecyl)ether ($C_{12}E_8$) (Nikko Chemicals (Tokyo)) in a buffer containing 7.9 mg NaCl/ml, 4.4 mg/ml trisodiumcitrate dihydrate, 2.1 mg/ml 2-morpholinoethane sulfonic acid monohydrate (MES) and 1.2 mg/ml N-hydroxy-ethyl-piperazine-N'-2-ethane sulfonic acid in $H_2O$ (pH adjusted with 1N NaOH to 7.3). The mixture was centrifuged at 170'000×g for 30 min. and the supernatant containing the influenza spike proteins (HA) and viral phospholipids was added to the above milky phospholipid mixture.

The whole suspension was stirred for at least one hour at low temperature (4° C). Subsequently, the suspension was applied to a Sephadex G-50 (of medium particle size) column (80×15 cm) which was equilibrated and eluted with the same buffer as used for the preparation of the phospholipid dispersion at 4° C. (flow rate 320 ml/h). The column was embedded in a water bath connected with an ultrasonification apparatus (Bransonic, Branson Europe BV, frequency 50 kHz±10%). 10 seconds of ultrasonic shocks repeated every minute yielded small unilamellar IRIVs. The sample volumes and column dimensions were such that a complete separation of IRIVs eluted at the void volume $V_o$ and cholate micelles was achieved. The retention of cholate was tested with $^3H$-labelled cholate (NEN Chemicals). After the first Sephadex G-50 chromatography less than 1% of cholate was retained yielding a phospholipid/cholate molar ratio of >50. A second chromatography dialysis for 12 hours at 4° C. reduced the cholate amount below the limit of detection, yielding phospholipid/cholate ratios >500 (i.e. less than 10 cholate molecules/IRIV). Absence of residual $C_{12}E_8$ was tested by a conventional hemolysis test: The amount was below the limit of detection (>100 nM). The IRIVs (FIG. 1) showed a mean diameter of about 100 nm and were conjugated with the HAV antigen in the following manner: A purified and inactivated HAV suspension, strain RG-SB XA112 (CNCMI-1080), containing 1 mg of HAV antigen, was pelleted by ultracentrifugation (4 h, 100'000× g). The IRIVs prepared above were added to the pellet. After resuspension the suspension was stirred at 20° C over night (16 hours). The HAV antigen spontaneously adsorbed by Vander-Waals forces onto the surface of IRIVs.

(B) Purified influenza virus A/Singapore/6/86 was stabilized in a buffer containing 0.1M octaethyleneglycol mono(n-dodecyl)ether (Nikko Chemicals, Tokyo, Japan), 7.9 mg/ml NaCl, 4.4 mg/ml trisodium citrate dihydrate, 2.1 mg/ml MES and 1.2 mg/ml N-hydaxylethyl-piperazine-N'-2-ethane sulfonic acid, pH 7.3. This mixture was centrifuged at 100,000×g for 30 minutes and the HA-containing supernatant was saved.

Phosphatidylcholine (PC; Sigma Chemical Co., St. Louis, Mo.) and phosphatidylethanolamine (PE; Sigma) (75%:25% wt/wt) were suspended in 0.01M Tris—0.1M NaCl, pH 7.3, and homogenized. Recrystallized sodium cholate (Sigma) was added to a final concentration of 0.02M to disintegrate multilamellar structures. To this solution was added the HA-containing supernatant and the suspension stirred for 1 h at 4° C. The suspension was applied to a Sephadex G-50 column (Pharmacia Fine Chemicals, Uppsala, Sweden) equilibrated in 0.01M Tris—0.1M NaCl, pH 7.3. The sealed column was placed in a water bath. During elution ultrasonic shocks (50 KHz; 10 s/min) were passed through the water bath using an ultrasonification device (Bransonic, Branson Europe BV, The Netherlands). The void volume fractions, which contained the IRIV, were pooled and re-chromatographed under identical conditions. The IRIV possessed an average diameter of approximately 150 nm.

The purified, inactivated HAV suspension with a known amount of antigen was centrifuged for 4 h at 100,000×g to pellet the virus. An appropriate quantity of the IRIV suspension was added to the pellet and gently resuspended by shaking. The suspension was gently stirred at 20° C. for 48 h to allow the HAV to adsorb onto the surface of the IRIV. This bulk suspension was diluted with sterile phosphate buffered saline, pH 7.4, to a final concentration of 2 μg HAV antigen/ml and bottled.

EXAMPLE 2

Preparation of IRIVs with HAV antigen crosslinked to the membrane

The preparation of IRIVs with crosslinked HAV antigens is schematically shown in FIG. 2.

The IRIVs were prepared according to Example 1 with the following modifications:

The HAV antigen molecules were attached to the IRIVs with a suitable crosslinker molecule. The following procedures were employed:

(A) Phosphoethanolamine (PE) was coupled with N-succinimidylpyridyl dithiopropionate (SPDP, Pierce) as follows: 15 mg of PE (20 μmol) was dried down in a 5 ml glass bottle. The dried PE was redissolved in 2 ml of dry chloroform (dried over a molecular sieve). Then 30 μmol of triethylamine (TEA) (3 mg), followed by 30 μmol of SPDP (10 mg) in 1 ml of dried methanol were added. The mixture was then stirred at room temperature under nitrogen for 1–2 hours until the reaction was complete (i.e. no more free PE). The reaction product was dried down on a rotary evaporator. The dried lipids were resuspended in chloroform and were immediately applied on the top of a silicic acid chromatography column, which had been prepared as follows: 2 g of silicic acid were dissolved in 10 ml of chloroform. The solution was poured into a 10 ml plastic syringe barrel plugged with glass fibre. The surplus was allowed to drain out and the syringe barrel was fitted with a plastic disposable three-way tap. After application of the lipids, the column was washed with 4 ml of chloroform. Finally, the column was eluted with 4 ml portions of a series of chloroform-methanol mixtures, first 4:0.25 [v/v] followed by 4:0.5 [v/v], 4:0.75 [v/v] and finally 4:1 [v/v] and 2 ml fractions were collected. The pure derivative was then located by thin-layer chromatography (TLC) using silica gel plates developed with chloroform-methanol-water (65:25:4 by vol.). The derivative runs faster than free PE and the spots are visualized by phosphomolybdate or iodine.

The fractions containing the desired product were pooled and concentrated by evaporation at reduced pressure in a rotary evaporator.

(B) The HAV antigen was thiolated by the following procedure: 5 ml of purified and inactivated HAV was dissolved in 0.1M phosphate buffer (PBS (pH 7.5)) at a concentration of 5 mg/ml$^{-1}$. Then, a SPDP solution at a concentration of 20 μmol$^{-1}$ (6 mg/ml$^{-1}$) in ethanol was mixed and 150 μl thereof was under stirring slowly added to 5 ml of the HAV protein solution with a Hamilton syringe to give a molar ratio of SPDP to protein of 15:1. The ethanol concentration was kept below 5% to prevent protein denaturation. The mixture was allowed to react for 30 min. at room temperature (20° C.). After the reaction was stopped, the protein was separated from the reactants by gel chromatography on Sephadex G-50, equilibrated with a solution containing 0.05M sodium citrate ($Na_3C_6H_5O_7$. $2H_2O$, 19.7 g . $1^{-1}$), 0.05M sodium phosphate ($Na_2HPO_4$. $7H_2O$, 13.4 g . $1^{-1}$), and 0.05M sodium chloride (2.9 g . $1^{-1}$) pH 7.0.

(C) The pretreated IRIVs and HAV antigens were coupled in the following manner: The IRIVs were prepared as in Example 1. Instead of PE the PE-SPDP was used. The HAV—SPDP was reduced as follows: The pH of the HAV—SPDP—solution in citrate-phosphate buffer was adjusted to pH 5.5 by the addition of 1M HCl. 10 μl of a DTT solution, 2.5M dithiothreitol (DTT, 380 mg/ml) in 0.2M acetate buffer, pH 5.5 (165 mg of sodium acetate in 10 ml) was added for each ml of protein solution. The solution was allowed to stand for 30 min. Subsequently, the protein was separated from the DTT by chromatography on a Sephadex G-50 column equilibrated with a PBS buffer, pH 7.0. In order to prevent oxidation of thiols all buffers were bubbled with nitrogen to remove oxygen. The protein fractions were also collected under nitrogen.

Finally, the IRIVs were mixed with the thiolated protein by stirring over night at room temperature.

EXAMPLE 3

Preparation of IRIVs with reduced HAV antigen

The IRIVs were prepared as in Example 2 with the following modifications: HAV antigen was not coupled with SPDP, but the disulphide bridges already present at the surface of the VP1 protein were used as precursors for free thiol groups. This conversion to free thiol groups was carried out as follows: 5 ml of an HAV solution were prepared in 0.1M phosphate buffer, pH 7.4 at a final antigen concentration of 5 mg/ml. For each ml of this solution, 10 μl of a DTT solution (prepared as described in Example 2) were added. The mixture was allowed to stand for 30 min. Then the protein was separated from the DTT by chromatography on a Sephadex G-50 column equilibrated with a PBS buffer at pH 7.0. Protein fractions were collected under nitrogen and were mixed with the IRIVs of Example 2.

EXAMPLE 4

Preparation of IRIVs containing HAV antigen

The IRIVs were prepared according to Example 1 with the following modification. 1 mg of purified and inactivated HAV in suspension was added to a pellet of purified influenza virus 90 A/Taiwan (0.002M of viral membrane phospholipids) and incorporated into the IRIVs by the method described in Example 1.

EXAMPLE 5

Production of an HAV-IRIV vaccine

HAV-IRIVs were prepared according to Examples 1, 2, 3 or 4 and diluted in PBS, pH 7.4 to a final concentration of 500 ng HAV protein $ml^{-1}$. This bulk solution was sterile filtrated through a membrane filter of pore size 0.2 μm (Millipore). A preservative (thiomersal) was added to a final dilution of $10^{-4}$. Aliquots of 0.6 ml of the final bulk vaccine were filled into vaccine vials under sterile conditions. Safety and potency tests were performed according to international regulations.

EXAMPLE 6

Preparation of an anti-idiotype IRIV vaccine against hepatitis C

The antigen-binding sites of antibody molecules (Ab1), also known as idiotypes, have been shown to induce the production of antibodies (anti-idiotypes, or Ab2). Because inoculation of animals with some Ab2 results in the production of antibodies (Ab3) that resemble Ab1 in their ability to bind antigen, it has been assumed that the binding sites of Ab2 act as a "mirror image" of the antigenic determinants originally recognized by Ab1 (and subsequently by Ab3 [Jerne, N. K., Ann. Immunol. (Paris) 125 C (1974), 373]. The major advantage of using anti-Id antibodies (Ab2) for eliciting antigen-specfic antibodies (Ab3) is that the vaccine recipient is never in contact with infectious agents or materials containing foreign genes.

The anti-idiotype IRIV vaccine against hepatitis C was prepared as follows: Sheep were immunized with an $Ab_1$ (dissolved of a concentration of 1 mg/ml in PBS) according to the following schedule: On day 0 the animals received 4 doses of 2 ml i.m. at different sites (thighs). On days 7, 14 and 28 they received 2 doses of 2 ml into both hindlegs. On day 42 350 ml of blood was collected from each sheep. The serum fraction was separated and further purified by conventional techniques (for a review, see Glück, R. and Labert, D.; Laboratory techniques in rabies, WHO, 4th edition, 1991, in press).

The purified anti-Id hepatitis C antibody was cleaved by digestion with pepsin and the resulting $F(ab')_2$ fragment was reduced with DTT (see Example 2) to yield 2 Fab' fragments. These Fab' fragments contained free sulphhydryl groups which reacted directly with the IRIVs of Example 2. This preparation was diluted to a protein concentration of 50 μg/ml with PBS, pH 7.4, and portioned in 0.6 ml aliquots in vaccine vials.

EXAMPLE 7

Safety and Immunogenicity of Inactivated Hepatitis A Vaccines: Comparision of IRIV-HAV prepared according to Example 1 with Alum-absorbed Vaccine (A) Hepatitis A virus (HAV) was purified after growth on MRC-5 human diploid cells (available from the American Type Culture Collection under accession number ATCC CCL 171). The virus was inactivated by treatment with formaldehyde (0.05%) at 37° C. for 10 days. Two vaccine series were tested. Vaccine series 1 consisted of inactivated virus linked to IRIVs according to Example 1 (A) (IRIV-HAV). Vaccine of series 2 was an alumadsorbed preparation containing 0.4% $Al(OH)_3$ (Al-HAV). Both vaccines contained 150 ng of HAV antigen per 0.5 ml dose. Seronegative adult volunteers (two groups of 15 persons each) received two intramuscular injections on day 0 and a booster injection on day 7 into the deltoid region. No systemic reaction or alterations in the blood chemistry were detected. With respect to local reactions, IRIV preparations provoked a significantly lower percentage of reactions than the alum-absorbed vaccine. The results of these experiments are summarized in FIG. 3.

It was also found that the IRIV preparations were more immunogenic than the alum preparation. To test the anti-HAV immune response, blood samples were taken from the volunteers on days 21 and 28 after the last injection. Sera were tested for HAV specific antibodies using a commercially available RIA (Abbott). The results are summarized in FIG. 4. The numbers on the columns represent the range of the anti-HAV antibody titer. Thus, the range of the anti-HAV antibody titers for the IRIV and alum-adsorbed vaccine formulations on day 21 was 82–988 and 69–844, respectively. The geometric mean titer (range) for the IRIV and alum-adsorbed vaccine formulations on day 28 was 453 mIU/ml (92–1210) and 361 mIU/ml (60–929), respectively. Thus, the IRIV preparations of the present invention are superior to alum-adsorbed vaccines.

(B) In a phase I clinical study with 120 human volunteers it could be demonstrated that one single IRIV adjuvanted hepatitis A vaccine dose induced protective antibody titers against hepatitis A which were 7 times higher than the antibody titer after the alum formulation. Up to now such a high immunopotentiation in man has never been achieved with any other liposomal, virosomal or immunosomal formulation due to the obvious lack of fully biologically active fusion peptides.

A total of 120 HAV seronegative (<10 mIU/ml) healthy adults were randomized to receive either fluid, alumadsorbed, or IRIV vaccine according to Example 1 (B). The vaccine (0.5 ml) was administered intramuscularly into the deltoid region. Volunteers were observed for approximately 30 minutes after vaccination for immediate-type reactions. Each volunteer was asked to record all adverse reactions on a report sheet for the 4 days following immunization. Serum samples for anti-HAV antibody determinations were taken at the time of immunization and 14 days later. Each vaccine formulation contained 1 μg of HAV antigen per 0.5 ml dose. One dose of the IRIV-HAV formulation also contained 10 μg of influenza HA and 125 μg total phospholipids. All three vaccines were found to be sterile and nontoxic for animals by standard test methods. In addition, all 3 formulations elicited a good anti-HAV antibody response in laboratory animals.

Each formulation was administered intramuscularly to 40 healthy adult volunteers seronegative for HAV antibody. The groups were well matched in regard to age and sex. Adverse reactions associated with immunization are shown in Table I. Pain at the injection site was the most frequently reported complaint with all the vaccines. Such discomfort was classified as moderate by one vaccine (2.5%) who received the fluid formulation, 9 (23%) who were immunized with the alum-adsorbed vaccine, and one (2.5%) who received the IRIV preparation. Severe pain was reported by one subject who received the alum-adsorbed vaccine. All other subjects who reported a "painful" reaction graded it as mild. Immunization with the alum-adsorbed vaccine was associated with a significantly ($P<0.01$) higher incidence of both pain and swelling/induration as compared to either the fluid or IRIV formulations. No systemic reactions attributable to vaccination were noted.

The anti-HAV antibody response engendered 14 days after vaccination is shown in Table II. Immunization with the fluid vaccine yielded a geometric mean titer (GMT) of 15.7 mIU/ml with 30% of subjects seroconverting (≧20 mIU/ml). While the alum-adsorbed vaccine induced both a modestly higher GMT (21.3 mIU/ml) and seroconversion rate (44%), neither was significantly greater than that obtained with the fluid vaccine. In contrast, the IRIV vaccine formulation elicited a far more vigorous antibody response. The GMT of 139.8 was significantly ($P<0.0001$) higher compared to either of the other two vaccines. All but one vaccine possessed ≧100 mIU/ml. Of greater importance was the fact that all vaccines seroconverted by day 14 compared to less than 50% for the other vaccine formulations ($P<0.005$).

TABLE I

Adverse Reactions Associated with Immunization

| Vaccine | Local reactions (%) | | | Systemic reactions (%) | | |
|---|---|---|---|---|---|---|
| | Pain | Swelling/ Induration | Red-ness | Fever | Head-ache | Malaise |
| Fluid | 42* | 0‖ | 0 | 0 | 0 | 0 |
| $Al(OH)_3$-adsorbed | 88$^+$ | 23¶ | 0 | 0 | 0 | 0 |
| IRIV | 25§ | 5** | 0 | 0 | 0 | 0 |

$^+$ vs * or §: $P < 0.01$
¶ vs ‖ or **: $P < 0.01$

TABLE II

Immunogenicity of Fluid, $Al(OH)_3$-Adsorbed, and IRIV-Adjuvanted Hepatitis A Vaccines

| Vaccine | Geometric mean titer (range) in mIU/ml | | Seroconversion rate No. ≧20 |
|---|---|---|---|
| Formulation | Day 0 | Day 14 | mIU/total (%) |
| Fluid | <10 | 15.7 (<10–100)* | 12/40 (30%)‖ |
| $Al(OH)_3$-adsorbed | <10 | 21.3 (10–100)$^+$ | 18/40 (44%)¶ |
| IRIV-adjuvanted | <10 | 139.8 (25–300)§ | 40/40 (100%)** |

Subjects received a single dose of vaccine on day 0.
§ vs * or $^+$: $P < 0.0001$
**vs ‖ or ¶: $P < 0.005$

EXAMPLE 8

Biological fusion activity of different reconstituted influenza virosomes

To study the role of the influenza viral membrane components in the fusion reaction in detail, it is necessary to be able to manipulate these components. For this purpose a method is required for the isolation and reconstitution of the viral spike proteins, producing reconstituted virosomes with full biological fusion activity. Most of the methods that have been used to reconstitute viral envelopes are based on solubilization of the viral membrane with a detergent.

Several reconstituted influenza virus envelopes using different methods which are described in the literature have been prepared:

[A] A virosome according to Huang, R.T.C. et al. (Huang, R.T.C., Wahn, K., Klenk, H. D. and Rott, R., Virology 97 (1979), pp. 212–217) which was prepared using detergents with a high critical micelle concentration (c.m.c.) [e.g. octylglucoside].

[B] A virosome according to Kawasaki, K. et al. (Kawasaki, K., Sato, S. B. and Ohmiski, S. I., Biochem. Biophys. Acta 733 (1983), pp. 268–290) which was prepared using detergents with a low c.m.c. (e.g. Triton X-100).

[C] A virosome according to Hosoka, Y. et al. (Hosaka, Y., Yasuda, Y. and Fukai, K., J. Virol. 46 (1983), pp. 1014–1017) which was prepared using Nonidet P-40 as detergent.

[D] An IRIV as it has been described in Example 1.

In addition, the following controls have been prepared:

[E] A purified influenza virus suspension as positive control.

[F] PBS-NaCl, pH 7.4, as negative control.

From each reconstituted influenza virus envelope solution and the influenza virus control a concentration of 10 μg/ml hemagglutinin in bicarbonate-free RPMI 1640 medium, supplemented with 10 mM NaCl (pH 7.4) was prepared. The negative control (PBS-NaCl) was diluted in the same medium 1:10. For the vesicle binding and fusion experiment MRC-5 human diploid fibroblasts were grown in 12-well cluster dishes (NUNC). The cells were seeded at 34,000 cells/ml per well and were used 3 days later. At this time, they were approximately 70–80% confluent.

0.5 ml of the reconstituted envelope solutions were added per well, for each preparation 20 wells. The vesicles were allowed to bind to the cells for 30 minutes at room temperature. During this incubation period the dishes were spun twice for 3 minutes at 500 g with a 180° rotation between spins. The centrifugation step enhances the binding of vesicles about 3-fold. After this 30-minute period the cells were washed four times with PBS-NaCl, pH 7.4, to remove unbound vesicles. For the fusion experiment, the fusion activity of the five preparations was induced by adding a fusion medium (RPMI 1640, supplemented with 10 mM succinate, 0.2% bovine serum albumin and 35 mM NaCl, pH 5.0) to each well (0.5 ml/well). After one minute, in two wells per preparation the fusion reaction was stopped by replacing the fusion medium with ethanol absolute. This was done every minute until 10 minutes had passed. The cells were then stained according to the method of May Gr ünwald-Giemsa:

The cells were then covered with an alcoholic May-Gr ünwald solution (Fluka No. 63590). After 5 minutes the cells were quickly washed with a phosphate buffer, pH 6.5, and stained with a Giemsa solution (Fluka No. 48900), diluted 1:10 with the same phosphate buffer. After another 10 minutes the cells were washed with running water: Under the microscope the cytoplasm of the cells appeared in a light blue color, the membranes in a dark blue color and the nuclei in a dark red color.

Under the microscope 10 sight fields were evaluated for counting the fused cells (containing at least two nuclei) and were calculated for each preparation and time interval. The FIG. 5 shows the mean value of two wells: It was obvious that only the IRIV preparation shared a fusion activity which was comparable to the influenza virus control. Preparation [B] yielded a fusion activity which was only around 30% compared to the positive control. The other preparations did not show any fusion activity (as the negative control did). From these results it can be concluded that only the described IRIVs show fully biological fusion activity, whereas the other methods for influenza envelope reconstitution do not yield vesicles with fusion activity and lead from a considerable to a complete loss of fusion activity.

We claim:

1. An immunostimulating reconstituted influenza virosome (IRIV) comprising the following components:
   (a) a mixture of phospholipids;
   (b) essentially reconstituted functional virus envelopes containing a trimeric influenza hemagglutinin protein (HA) or a peptide with the amino terminal 21 amino acid residue segment of $HA_2$ which has biological fusion activity equivalent to native HA at a pH value of about 5.0 wherein said biological fusion activity induces the fusion of said IRIV with cellular membranes and the lysis of said IRIV after endocytosis by antigen presenting cells; and
   (c) a whole, inactivated hepatitis A virus (HAV), said virus being attached or adsorbed to the surface of the IRIV;

wherein the IRIV is substantially unilamellar.

2. The IRIV according to claim 1, wherein the essentially reconstituted virus envelopes contain a peptide with the amino terminal 21 amino acid residue segment of $HA_2$.

3. The IRIV according to claim 1, wherein said essentially reconstituted functional virus envelopes are in the form of a unilamellar bilayer.

4. The IRIV according to claim 1, wherein the HAV is hepatitis A virus strain RG-SB XA112 (CNCM I-1080).

5. The IRIV according to claim 1, wherein said mixture comprises phosphatidylcholine and phosphatidylethanolamine.

6. The IRIV according to claim 5, wherein phosphatidylcholine and phosphatidylethanolamine are in a weight ratio of 4:1.

7. The IRIV according to claim 1, wherein the weight ratio of a mixture of phospholipids:essentially reconstituted functional virus envelopes is from about 1:1 to about 20:1.

8. A vaccine containing an IRIV according to claim 1 optionally in combination with a suitable pharmacologically acceptable carrier and/or diluent.

9. A method of stimulating the immune system of a patient in need thereof comprising administering a suitable dosage for providing a protective immune response of an IRIV according to claim 1.

10. A method for the prophylaxis of hepatitis A infections comprising administering a suitable dosage for providing a protective immune response of an IRIV according to claim 1 to a patient in need thereof.

* * * * *

UNITED STATES PATENT AND TRADEMARK OFFICE

CERTIFICATE OF CORRECTION

PATENT NO. : 5,565,203

DATED : October 15, 1996

INVENTOR(S) : Reinhard Glück and Robert Mischler

It is certified that error appears in the above-identified patent and that said Letters Patent is hereby corrected as shown below:

On the title page:

Attorney, Agent, or Firm --Greenblum & Bernstein, P.L.C.
is in error and should be as follows:
Attorney, Agent, or Firm --Fish & Richardson P.C.

Signed and Sealed this

Eleventh Day of February, 1997

Attest:

BRUCE LEHMAN

Attesting Officer

Commissioner of Patents and Trademarks